United States Patent [19]
Flohr
[11] Patent Number: 4,808,328
[45] Date of Patent: Feb. 28, 1989

[54] IODINE-BASED ANTISEPTIC CLEANSER COMPOSITION

[75] Inventor: Keith W. Flohr, Reston, Va.
[73] Assignee: Joseph N. Cooper, Alexandria, Va.

[21] Appl. No.: 47,345
[22] Filed: May 8, 1987
[51] Int. Cl.[4] ........................ C11D 3/02; C11D 3/48; A61K 33/18
[52] U.S. Cl. .................................... 252/106; 424/150; 252/DIG. 14
[58] Field of Search ................. 252/106, 107; 424/150

[56] References Cited

U.S. PATENT DOCUMENTS

| | | | |
|---|---|---|---|
| 3,525,696 | 8/1970 | Schmidt et al. | 252/106 |
| 3,917,822 | 11/1975 | Turney | 424/150 |
| 4,045,364 | 8/1977 | Richter | 252/106 |
| 4,148,884 | 4/1979 | Thorogood | 424/150 |
| 4,207,310 | 6/1980 | Langford | 424/150 |
| 4,271,149 | 6/1981 | Winicov et al. | 424/150 |
| 4,387,217 | 6/1983 | Schmolka | 528/417 |

*Primary Examiner*—Prince E. Willis
*Attorney, Agent, or Firm*—Sughrue, Mion, Zinn, Macpeak, and Seas

[57] ABSTRACT

A concentrated antiseptic cleanser composition for use on an industrial scale is disclosed, comprising effective amounts of iodine as the antiseptic agent and an organic detergent (preferably sodium lauryl sulfonate) as the cleansing agent, an alcoholic solvent, preferably isopropanol, a buffer, preferably sodium borate decahydrate, and a chelating agent preferably tetrasodium EDTA. A mild abrasive cleansing agent and a fragrant also may be present. Water is present in an inverse relationship on a volume percent basis with the lower alcohol solvent. The pH of the composition ranges from about 7.9 to 8.5. This concentrated composition demonstrates superior antiseptic and cleansing properties, and is useful on a wide variety of surfaces, most commonly used in public restrooms and the like.

10 Claims, No Drawings

IODINE-BASED ANTISEPTIC CLEANSER COMPOSITION

FIELD OF THE INVENTION

The present invention relates to a concentrated antiseptic cleanser composition, intended primarily for use on an industrial scale, particularly for cleaning and disinfecting public restrooms and the like. The present invention demonstrates excellent cleansing as well as antiseptic or disinfectant properties, and is effective at dilutions of up to about 50:1 for certain applications, thus being economical to use as well.

BACKGROUND OF THE INVENTION

Many cleansing or detergent compositions are known, as are various antiseptic disinfecting agents. Moreover, certain compositions comprising a cleanser/detergent and an antiseptic agent in combination are known. Two specific examples of such a composition comprising a cleanser/antiseptic agent which are readily commercially available are Lysol® (a trademark of Lehn & Fink Products, a Division of Sterling Drug) and PineSol® (a trademark of American Cyanamid Company), and these compositions are generally effective for most ordinary household cleansing/disinfecting purposes. However, neither or these compositions exhibits the degree of antiseptic activity which is required to properly sanitize and disinfect public restrooms where the presence of various bacteria and viruses is generally more of a problem, and can lead to public health concerns if such microbial growth is not kept under control.

U.S. Pat. No. 3,654,165 discloses a telephone cleaner-sanitizer composition which employs iodine as the bactericidal agent and sodium lauryl sulfate as the detergent in combination with dimethyl sulfone. Isopropanol is disclosed as the solvent. However, such a cleaner-sanitizer composition is stated to be quick-drying, thus employing large amounts of iso-propanol to effect this purpose; moreover, iodine is present in relatively small amounts, i.e., substantially less than 1 wt per vol %. Thus, this low-iodine, quick-drying telephone cleaner-sanitizer compositions disclosed in U.S. Pat. No. 3,654,165 would not be effective for industrial disinfecting and cleansing, such as in public restrooms, which require strong antimicrobial and scrubbing action.

Thus, while iodine is known to have antiseptic or sanitizing properties, a concentrated composition such as the present invention employing relatively large amounts of iodine in combination with an organic detergent in an alcohol-based solvent and also containing a buffer and a chelant, capable of superior antimicrobial activity, is believed to be novel.

SUMMARY OF THE INVENTION

Accordingly, one object of the present invention is to provide a concentrated antiseptic cleanser composition for industrial usage which exhibits superior antimicrobial effects and cleansing properties, including grease-cutting ability.

Another object of the present invention is to provide a concentrated antiseptic cleanser composition which retains its antimicrobial and cleansing properties for an extended period of time, i.e., has an extended shelf life.

A further object of the present invention is to provide a concentrated antiseptic cleanser composition which can be used in diluted form for various applications, and thus is economical to use.

Still another object of the present invention is to provide a concentrated antiseptic cleanser composition which has a pleasant fragrance, does not leave behind a residual film, and will not stain the applicator's hands.

The above and other objects and advantages of the present invention can be satisfied by the antiseptic cleanser composition described below, i.e., an antiseptic cleanser composition comprising:

(a) about 1.0–10% (wt per vol) of iodine as an antiseptic agent;
(b) about 2.0–10.0% (wt per vol) of an organic detergent as a cleansing agent;
(c) about 20.0–60.0 vol % of a lower alcohol as a solvent;
(d) about 0.01–3.0% (wt per vol) of a buffer;
(e) about 0.01–1.0% (wt per vol) of a chelating agent;
(f) 0 to about 1.5% (wt per vol) of a mild abrasive cleansing agent;
(g) 0 to about 15% (wt per vol) of a fragrance; and,
(h) the remainder, water by vol %, wherein the pH of the composition is from about 7.9 to about 8.5.

DETAILED DESCRIPTION OF THE INVENTION

Iodine is used in the antiseptic cleanser composition as the antiseptic or disinfecting ingredient. Iodine exhibits excellent antimicrobial effects against a wide range of microorganisms. As shown in the Example described hereafter, when employed in relatively large amounts as in the present invention, iodine exhibits superior antimicrobial effects when compared to other antiseptic agents used in commercially available antiseptic/-cleanser compositions, such as Lysol® and PineSol®.

Further, iodine may be characterized as environmentally benign, i.e., there are no known adverse side effects to using iodine as the antiseptic agent. Also, since iodine is very reactive and has a high vapor pressure, the selection of the lower alcohol-based solvent keeps the iodine in solution and reduces the iodine vapor pressure. Another advantage of employing iodine as the antiseptic agent is that iodine leaves substantially no film or residue after its application to the surfaces to be disinfected. Other antiseptic agents are known to leave a residue or film on the surfaces after application, and such a residue or film may cause microorganisms to become resistant to the residual disinfectant. Thus, using iodine as the antiseptic agent would effectively eliminate this possibility.

Iodine is present in the antiseptic cleanser composition in an amount of from about 1.0 to about 10.0 wt per vol %, preferably from 2.0 to 5.0 wt per vol %, and most preferably 3.0 wt per vol %.

The organic detergent employed as a cleaning agent in the present invention can be selected from among known organic sulfonates, such as sodium lauryl sulfonate. However, naphthalene sulfonate has been determined to cause the formation of precipitates in the solution; thus, its use should be avoided. The amount of cleansing agent present in the composition should be in an inverse relationship with respect to the amount of the alcoholic solvent, but, of course, both must be within the amounts defined below. The composition contains from about 2.0 to about 10.0 wt per vol % of the organic detergent, preferably from 3.0 to 7.0 wt per vol %, and most preferably 5.0 wt per vol %. Sodium lauryl sulfonate is the most preferred organic detergent suitable for use as the cleansing agent in the present invention.

The lower alcohol-based solvent is suitably selected from among methanol, ethanol, propanol and iso-propanol. Iso-propanol is the most preferred solvent. The alcoholic solvent is present in the composition in an amount of from about 20.0 to about 60.0 vol %, preferably 40.0 to 55.0 vol %, most preferably 50.0 vol %. As noted, if a higher amount of solvent within this range is present in the composition, the amount of the organic detergent should be proportionately lowered within the abovedescribed range of 2.0–10.0 wt per vol %. When the alcoholic solvent is used within this range, the composition is not characterized as "quick-drying", but rather, exhibits better cleansing properties due to its increased scrubbing time. If the alcoholic solvent were present in amounts greater than about 60.0 vol %, a fast-drying composition would result, inherently having poorer cleansing ability. The alcoholic solvent helps cut grease and oil which may be present on the surfaces to be cleaned/disinfected with the composition of the present invention, and thus, the selection of an alcoholic solvent as the cleansing agent aids in the cleansing properties of the composition as a whole.

The buffer is preferably selected from among sodium borate decahydrate and trisodium phosphate, and is present in the composition in an amount of from about 0.01 to about 3.0 wt per vol %, preferably 1.0 to 3.0 wt per vol %, and most preferably 2.0 wt per vol %. The buffer should be present in a sufficient amount within this range so that the pH of the composition is from about 7.9 to about 8.5, most preferably about 8.2. The present invention has been determined to be more effective at such a slightly basic or alkaline pH as to its cleansing ability; a slightly alkaline pH also aids in stabilizing the composition. Moreover, sodium borate decahydrate and trisodium phosphate also can be characterized as mild cleansing agents/mild disinfectants and thus aid in the composition's ability to perform its intended cleansing and disinfecting functions. Sodium borate decahydrate is the most preferred buffer.

A water softener or chelating agent is also present in the composition, which is effective to tie up any metal ions which may be present (e.g., $Ca^{++}$, $Mg^{++}$). The chelating agent also acts as a sum remover, which is helpful when the composition of the present invention is used to clean bathroom tiles, tubs, basins, sinks, etc. The chelating agent may be present an in amount from about 0.01 to about 1.0 wt per vol %, preferably 0.2 to 0.7 wt per vol %, and most preferably 0.5 wt per vol %. Tetrasodium ethylenediamine tetraacetic acid (EDTA) and nitrilotriacetic acid (NTA) are examples of suitable chelating agents; tetrasodium EDTA is most preferred.

A mild abrasive cleansing agent may also be added to the composition, such as sodium metasilicate, which may be present in an amount up to about 1.5 wt per vol %, preferably 0.5 to 1.2 wt per vol %, and most preferably 1.0 wt per vol %. The addition of the mild abrasive cleansing agent is desirable since its presence aids in the general cleansing properties of the composition, and also acts as a mild abrasive on a microscopic scale; i.e., sodium metasilicate, for example, exhibits excellent cleansing results due to its mild abrasive ability on microporous surfaces, such as porcelain and certain tiles. Cesium oxide and alumina are other suitable mild abrasive cleansing agents, but sodium metasilicate is most preferred.

The antiseptic cleansing composition of the present invention may further contain a fragrant or odorant which may be present in an amount up to about 15% by volume, although lesser amounts of the fragrant are more preferred (e.g., 0.2 to 2.0 vol %), and amounts less than 1 vol % are even more preferred, 0.4 vol % being most preferred. The fragrant can be selected from among simple esters (i.e., acids containing 1 to 5 carbon atoms linked with alcohols containing 2 to 4 carbon atoms), such as ethyl butyrate and butyl acetate. Ethyl butyrate is the most preferred fragrant and additionally acts as a grease or oil cutter, thus further aiding the cleansing properties of the composition.

The remainder of the antiseptic cleanser composition is water, calculated on a volume percent basis. A composition containing the above ingredients within the recited ranges as to suitable amounts for each would be considered as a concentrated composition or solution.

In practical usage, however, the composition is preferably diluted by mixing it with water in amounts ranging from a dilution of about 1:1 for spot cleaning to about 50 parts water per 1 part concentrated composition for cleaning floors. Intermediate dilutions can be used for other surfaces, as necessary, depending on the condition of the surface with respect to the amount of dirt, grime, microorganisms, etc., as well as the physical characteristics of the surface itself, i.e., whether such is relatively smooth or porous. In general, for generally effectively cleaning and disinfecting an average public restroom or the like, a dilution of 9 parts water to 1 part concentrated composition is suitable.

The composition should also not be used near ammonium hydroxide ($NH_4OH$), since contact explosions might occur upon reaction ($NH_4OH$), since contact explosions might occur upon reaction with the composition.

Another advantage of the present invention is that the concentrated composition described above has an excellent shelf life, retaining its cleansing and disinfecting properties for at least twelve months or longer without undergoing decomposition.

The most preferred embodiment of the antiseptic cleanser composition in accordance with the present invention comprises:

(a) 3.0% (wt per vol) iodine;
(b) 5.0% (wt per vol) sodium lauryl sulfonate;
(c) iso-propanol present in an equal volume with water (approximately 50 vol % of each);
(d) 2.0% (wt per vol) sodium borate decahydrate;
(e) 0.5% (wt per vol) tetrasodium EDTA;
(f) 1.0% (wt per vol) sodium metasilicate; and
(g) 0.4% (vol per vol) ethyl butyrate.

This specific composition within the scope of the present invention was prepared and labeled "A4", and was then tested as illustrated in the following Example to demonstrate the antimicrobial efficacy of this antiseptic cleanser composition; however, the following Example should not be construed as limiting the scope of the present invention in any manner.

EXAMPLE

Comparative testing was performed as outlined below to demonstrate the efficacy as to the antimicrobial properties of the present invention in comparison with commercially available antiseptic cleansing formulations. Composition A4 according to the present invention (described above), was tested at full-strength and at a dilution of 1 part concentrated A4 with 9 parts water against two commercially available antiseptic/cleansing compositions, Lysol® and PineSol®; in addition, a control formulation consisting of water alone was tested. The specific compositions and relative concentrations of each disinfecting composition are described as follows (dilutions are calculated by vol %):

(a) Full-strength A4
(b) 10% A4 : 90% $H_2O$
(c) Full-strength Lysol®
(d) 10% Lysol®: 90% $H_2O$
(e) 10% PineSol®: 90% $H_2O$
(f) 100% $H_2O$ Comparative testing was patterned after the "Standardized Disk-Agar Diffusion Method for Determining Susceptibility to Antibiotics", and was carried out in order to compare the present invention's antimicrobial efficacy to that of commercially available disinfectant compositions. Both Lysol® and PineSol® are recommended for usage at dilutions of 1 part concentrate per 9 parts $H_2O$; thus, A4 was diluted to the same concentration for purposes of comparison.

Four commonly encountered microorganisms were chosen for testing the antimicrobial activity of each formulation:

(1) *Staphylococcus aureus,* normally found on human skin and in human nasal passages, is a common cause of bacterial food poisoning. This organisms has also been implicated as a causative agent of Toxic Shock Syndrome.

(2) *Pseudomonas aeruginosa,* which is known to cause pneumonia, urinary, eye, and post-operative infections in humans, and can survive and even multiply in cool, moist environments often found in restrooms, such as toilets and their immediate surroundings.

(3) *Escherichia coli,* an organism which inhabits the human intestinal tract and thus is also normally present in restroom toilets and associated environments.

(4) *Streptococcus faecalis,* another organisms which commonly inhabits the human intestinal tract, causes septicemia (blood poisoning) as well as a variety of other infections, and is also commonly present in restroom environments, The above disinfectant ((a)–(f)) compositions were tested for antimicrobial effectiveness against each of these four microorganisms. First, petri dishes containing agar as the growth medium were smeared with an innoculation containing one of the four microorganisms, the smear covering the entire surface of the growth medium. A paper tape tab, having been saturated with one of the test solutions, was then placed in the center of each plate. The growth media were allowed to incubate for a period of approximately two days, after which the antimicrobial activity of each test solution was measured. A zone of complete inhibition is defined as the zone where no detectable bacterial growth occurred. A zone of partial inhibition is defined as the area which exhibits a reduction in the number of detectable bacterial colonies, as compared to the $H_2O$ (control) plate.

The zones of complete and partial inhibition were measured on each test plate, and the results are summarized in table form below:

TABLE 1

(Antimicrobial Activity vs. *Staphylococcus aureus*)

| Test Solution | Zone of Complete Inhibition (radius in mm) | Zone of Partial Inhibition (radius in mm) |
|---|---|---|
| (a) Full-strength A4 | 16 mm | 19 mm |
| (b) 10% A4:90% $H_2O$ | 7 mm | 10 mm |
| (c) Full-strength Lysol ® | 12 mm | 16 mm |
| (d) 10% Lysol ®:90% $H_2O$ | 6 mm | 8 mm |
| (e) 10% PineSol ®:90% $H_2O$ | 4 mm | 5 mm |
| (f) 100% $H_2O$ | 0 mm | 0 mm |

TABLE 2

(Antimicrobial Activity vs. *Pseudomonas Aeruginosa*)

| Test Solution | Zone of Complete Inhibition (radius in mm) | Zone of Partial Inhibition (radius in mm) |
|---|---|---|
| (a) Full-strength A4 | 18 mm | 28 mm |
| (b) 10% A4:90% $H_2O$ | 4 mm | 13 mm |
| (c) Full-strength Lysol ® | 5 mm | 5 mm |
| (d) 10% Lysol ®:90% $H_2O$ | 0 mm | 5 mm |
| (e) 10% PineSol ®:90% $H_2O$ | 0 mm | 25 mm |
| (f) 100% $H_2O$ | 0 mm | 0 mm |

TABLE 3

(Antimicrobial Activity vs. *Escherichia coli*)

| Test Solution | Zone of Complete Inhibition (radius in mm) | Zone of Partial Inhibition (radius in mm) |
|---|---|---|
| (a) Full-strength A4 | 15 mm | 22 mm |
| (b) 10% A4:90% $H_2O$ | 5 mm | 15 mm |
| (c) Full-strength Lysol ® | 10 mm | 12 mm |
| (d) 10% Lysol ®:90% $H_2O$ | 2 mm | 4 mm |
| (e) 10% PineSol ®:90% $H_2O$ | 2 mm | 6 mm |
| (f) 100% $H_2O$ | 0 mm | 0 mm |

TABLE 4

(Antimicrobial Activity vs. *Streptococcus faecalis*)

| Test Solution | Zone of Complete Inhibition (radius in mm) | Zone of Partial Inhibition (radius in mm) |
|---|---|---|
| (a) Full-strength A4 | 17 mm | 18 mm |
| (b) 10% A4:90% $H_2O$ | 13 mm | 15 mm |
| (c) Full-strength Lysol ®* | — | — |
| (d) 10% Lysol ®:90% $H_2O$ | 5 mm | 8 mm |
| (e) 10% PineSol ®:90% $H_2O$ | 9 mm | 9 mm |
| (f) 100% $H_2O$ | 0 mm | 0 mm |

*Test results were not available for this composition v. *S. faecalis.*

The four microorganisms tested above were obtained from the American Type Culture Collection, and are known strains commonly used in comparative growth inhibition testing. *S. aureus* is designated ATCC 12600; *P. aeruginosa* is designated ATCC 10145; *E. Coli* is designated ATCC 8677; and *S. faecalis* is designated ATCC 35550.

The results shown above in Tables 1–4 demonstrate the unexpectedly superior degree of antimicrobial activity that compositions prepared in accordance with the present invention are able to obtain. Full-strength A4 has been shown to exhibit outstanding antimicrobial activity against each of the four microorganisms commonly found in public restroom environments, and even when diluted with 9 parts water, the compositions made in accordance with the present invention demonstrated surprisingly superior antimicrobial efficacy as compared to test solutions comprising similar concentrations of commercially available disinfectant/cleansing compositions.

Having described the antiseptic cleanser composition of the present invention in detail, it will become apparent to those skilled in the art that various modifications may be made thereto without departing from the spirit and scope of the invention as defined in the claims below.

What is claimed is:

1. A concentrated antiseptic cleanser composition comprising:

(a) about 1.0 to about 10.0% (wt per vol) of iodine as an antiseptic agent;

(b) about 2.0 to about 10.0% (wt per vol) of an organic sulfonate detergent as a cleansing agent;

(c) about 20.0 to about 60.0 vol % of a lower alcohol as a solvent;

(d) about 0.01 to about 3.0% (wt per vol) of a buffer;

(e) about 0.01 to about 1.0% (wt per vol) of a chelating agent;

(f) 0 to about 1.5% (wt per vol) of a mild abrasive cleansing agent;

(g) 0 to about 15.0% (wt per vol) of a fragrance; and, (h) the remainder, water by vol %, wherein the pH of said composition is from about 7.9 to about 8.5.

2. A concentrated antiseptic cleanser composition as claimed in claim 1, wherein said organic detergent is sodium lauryl sulfonate, said lower alcohol is selected from iso-propanol, propanol, ethanol, and methanol, said buffer is selected from sodium borate decahydrate and trisodium phosphate, said chelating agent is selected from tetrasodium EDTA and nitrilotriacetic acid, said mild abrasive cleansing agent is selected from sodium metasilicate, cesium oxide and alumina, and said fragrance is selected from ethyl butyrate and butyl acetate.

3. A concentrated antiseptic cleanser composition as claimed in claim 1, wherein said organic detergent is sodium lauryl sulfonate, said lower alcohol is isopropanol, said buffer is sodium borate decahydrate, said chelating agent is tetrasodium EDTA, said mild abrasive cleansing agent is sodium metasilicate and said fragrance is ethyl butyrate.

4. A concentrated antiseptic cleanser composition as claimed in claim 1, comprising:

(a) 2.0 to 5.0% (wt per vol) of iodine as an antiseptic agent;

(b) 3.0 to 7.0% (wt per vol) of an organic detergent as a cleansing agent;

(c) 40.0 to 55.0 vol % of a lower alcohol as a solvent;

(d) 1.0 to 3.0% (wt per vol) of a buffer;

(e) 0.2 to 0.7% (wt per vol) of a chelating agent;

(f) 0.5 to 1.2% (wt per vol) of a mild abrasive cleansing agent;

(g) 0.2 to 2.0% (wt per vol) of a fragrance; and, (h) the remainder, water by vol %, wherein the pH of said composition is from about 8.0 to about 8.5.

5. A concentrated antiseptic cleanser composition as claimed in claim 4, wherein said organic detergent is sodium lauryl sulfonate, said lower alcohol is selected from the group consisting of iso-propanol, propanol, ethanol, and methanol, said buffer is selected from sodium borate decahydrate and trisodium phosphate, said chelating agent is selected from tetrasodium EDTA and nitrilotriacetic acid, said mild abrasive cleansing agent is selected from sodium metasilicate, cesium oxide and alumina, and said fragrance is selected from ethyl butyrate and butyl acetate.

6. A concentrated antiseptic cleanser composition as claimed in claim 5, wherein said organic detergent is sodium lauryl sulfonate, said lower alcohol is isopropanol, said buffer is sodium borate decahydrate, said chelating agent is tetrasodium EDTA, said mild abrasive cleansing agent is sodium metasilicate, and said fragrance is ethyl butyrate.

7. A concentrated antiseptic cleanser composition as in claim 1, wherein the concentrated composition is diluted with water.

8. A concentrated antiseptic cleanser composition as in claim 7, wherein said dilution ratio of the concentrated composition to water is about 1:1.

9. A concentrated antiseptic cleanser composition as in claim 7, wherein said dilution ratio is up to about 9 parts water to 1 part concentrated composition.

10. A concentrated antiseptic cleanser composition as in claim 7, wherein said dilution ratio is up to about 50 parts water to 1 part concentrated composition.

* * * * *